United States Patent [19]

Spademan

[11] Patent Number: 4,534,081
[45] Date of Patent: Aug. 13, 1985

[54] TOOTH CLEANING BRISTLE AND HOLDER

[76] Inventor: Richard G. Spademan, Box 6410, Incline Village, Nev. 89450

[21] Appl. No.: 583,200

[22] Filed: Feb. 24, 1984

Related U.S. Application Data

[63] Continuation-in-part of Ser. No. 509,000, Jun. 29, 1983, abandoned.

[51] Int. Cl.³ .............................................. A46B 9/04
[52] U.S. Cl. ................................... 15/167 R; 15/110; 15/159 A; 433/142; 128/62 A
[58] Field of Search ......................... 15/110, 186–188, 15/159 A, 167 R, 167 A, 176; 433/142, 143; 128/62 A; 132/89, 93

[56] References Cited

U.S. PATENT DOCUMENTS

| | | | |
|---|---|---|---|
| 2,354,780 | 8/1905 | Stewart | 128/62 A |
| 2,800,899 | 7/1957 | Barron | 15/167 R X |
| 3,660,902 | 5/1972 | Axelsson | 132/89 X |
| 4,205,664 | 6/1980 | Baccialon | 128/62 A |

Primary Examiner—Peter Feldman
Attorney, Agent, or Firm—Townsend and Townsend

[57] ABSTRACT

A toothbrush comprising an elongate, flexible, one-piece bristle 10 having a rounded end and textured with tooth cleansing elements 14 on the side of the bristle. A free end 18 of the bristle is thin enough to penetrate the space between the teeth and the gums. Opposite its free end, the bristle has a generally cylindrical stem 20. A toothbrush holder 50 is provided having a conventionally shaped handle end 52 and a tip end 54 defining a cylindrical opening 56. The cylindrical stem 20 of the bristle is rotatably engageable in the cylindrical opening 56 of the tip 54. In an alternative embodiment, the cleansing elements 14 are offset from and directed toward the toothbrush holder 50 pivot axis.

24 Claims, 17 Drawing Figures

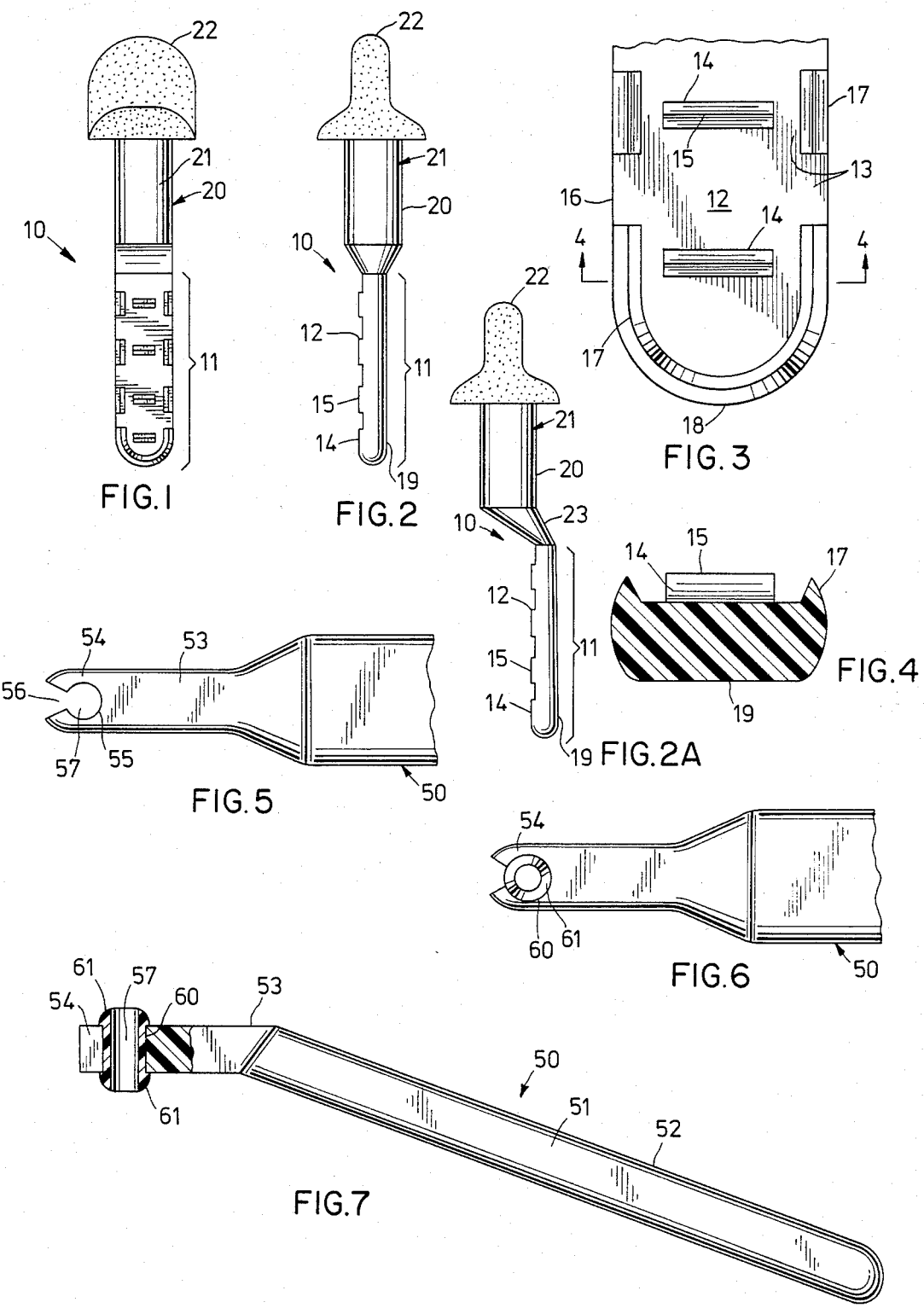

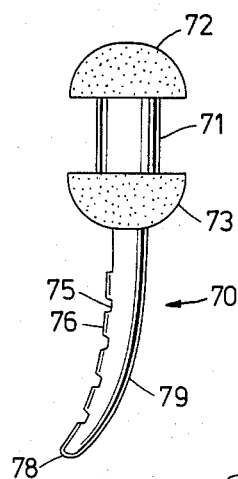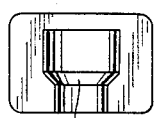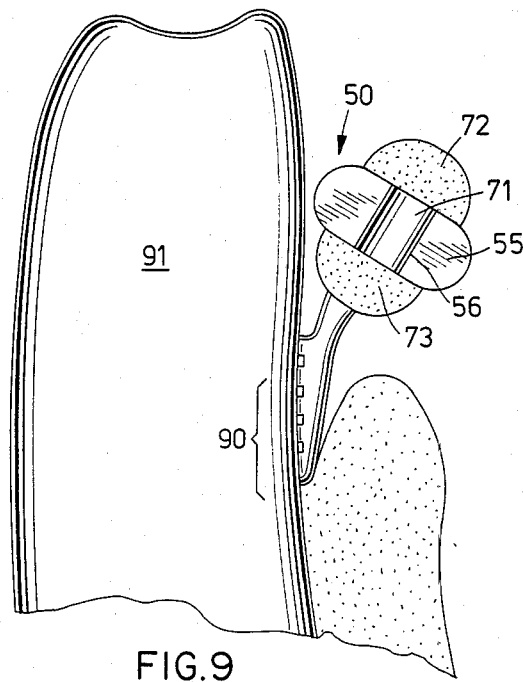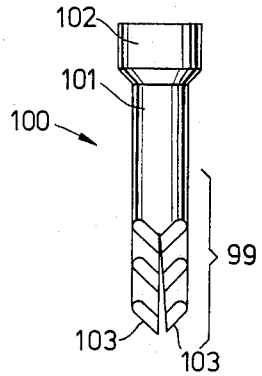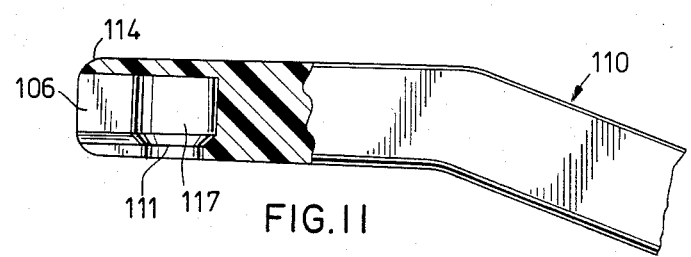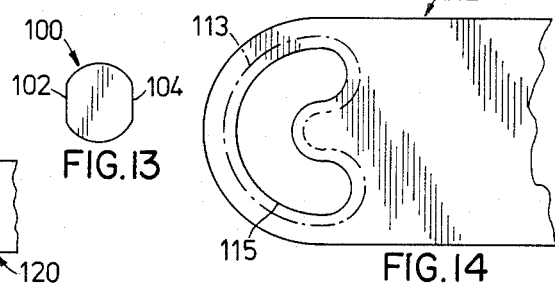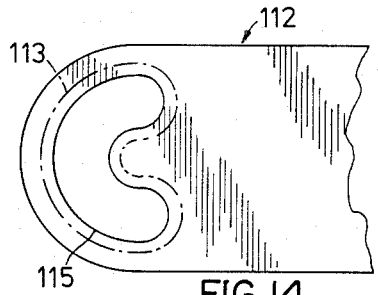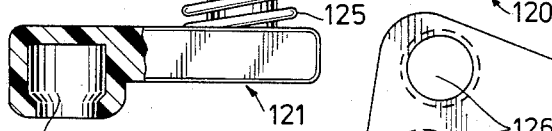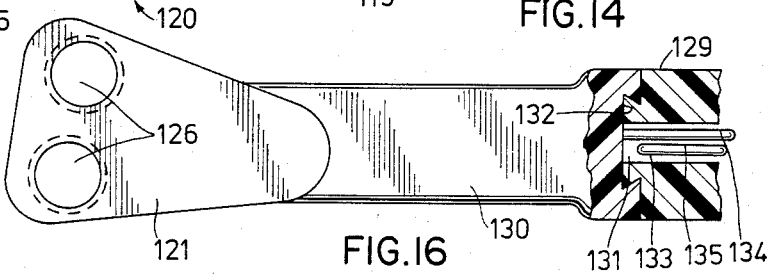

TOOTH CLEANING BRISTLE AND HOLDER

RELATED APPLICATION

The present application is a continuation-in-part of applicant's application Ser. No. 509,000 filed June 29, 1983 entitled "Tooth Cleaning Bristle and Holder", now abandoned.

BACKGROUND OF THE INVENTION

1. Field of the Invention

The present invention relates generally to toothbrushes and specifically to a toothbrush bristle and holder configuration providing better removal of microbial plaque accumulation from the exposed and subgingival surfaces of teeth.

2. Description of the Prior Art

Plaque control retards the formation of calculus and is critical in the prevention of periodontal disease. The development of gingival inflammation and dental cavities is usually caused by an accumulation of dental plaque on the subgingival tooth surfaces and, to a lesser extent, materia alba on the gingival surface in the subgingival space. Dental plaque is formed by oral microorganisms which synthesize harmful products that are destructive to the tooth and gum when not removed. Both dental plaque and materia alba can form within several hours, and therefore frequent mechanical cleansing is essential. Cleaning the narrow interproximal spaces between the teeth and the gingival sulcus surrounding the teeth is difficult with a conventional toothbrush. In addition to the problem of holding the toothbrush in the correct posture to enter these spaces, the sharp points of conventional toothbrush bristles can damage the gingiva in the interproximal embrasure and subgingival space when the bristle tips stray from the teeth surfaces. Studies show that the most aggressive mechanical cleaning should be directed toward the tooth surface, much less so toward the gingival surface and none toward the base of the gingival sulcus. The basis for these observations is as follows. Materia alba accumulation on the gingiva which consists primarily of an acquired bacterial coating and desquamated epithelial cells, leucocytes and a mixture of salivary proteins and lipids is a soft sticky deposit less adherent than dental plaque. It can be flushed away with a water spray but more completely removed from the gingiva with mild mechanical cleansing. Also, the gingiva can become sensitive to mechanical trauma because the toxins formed by oral microorganisms cause cellular damage to the gingiva with subsequent inflamation or gingivitis. When gingivitis occurs, vascular dilitation, capillary proliferation, engorged vessels and sluggish venous return causes a stretched and thinned epithelium that is sensitive to mechanical trauma such as aggressive brushing or abrasion from a sharp tooth pick or the like.

Dental plaque is harder and more adherent than materia alba. Removal requires much more aggressive mechanical cleansing than is required to remove materia alba from the gingiva. However, exposure of the root surface can occur due to faulty or aggressive brushing by repeated direct trauma to the base of the sulcus with the sharp point of a bristle or toothpick.

The teeth in a set are typically of different sizes and curvatures. Heretofore, the bristle supports of toothbrushes have typically been rigidly mounted to the end of the toothbrush handle, and the length and width of a conventional bristle support exceeds the distance between midpoints of adjacent teeth. The surfaces of the teeth in the interproximal embrasures are not contacted by the bristles of the bristle support, particularly if the bristles are stiff.

Another disadvantage of prior toothbrushes is that it is difficult to clean the subgingival surfaces of the teeth by the "up and down" motion of conventional toothbrushing. This is because the sulcus is relatively shallow and it is difficult while brushing one's teeth to judge how deeply to penetrate the sulcus before injuring the base of the sulcus. Consequently, there is a tendency to avoid penetrating the sulcus.

Because the teeth and gingiva have poor sensory perception, the user of a toothbrush must rely on the brush design to assure proper position and pressure of the cleansing elements against the tooth surfaces.

A variety of cleaning devices are available to remove the plaque and soft debris not easily accessible to conventional toothbrushes. Dental floss is used to clean these areas, although the proper application of floss requires considerable manual dexterity. Further, concave root surfaces cannot be reached with dental floss. Toothpicks or the like can be used with or without holders, as disclosed in U.S. Pat. No. 3,892,040. The small tip of a tooth pick allows good tooth visibility. However, the sharp point and lack of cleaning edges on the side of the toothpick prevent efficient cleaning, while presenting a potential for gingival damage. An apparatus for cleansing adjacent faces of the teeth as disclosed in U.S. Pat. No. 3,660,902, has a rotatable engagement of the cleansing tool and handle to assist in tooth contact but the point and opposite abrading faces of the tool can damage the gingival sulcus and adjacent gingival surface.

Interdental brushes such as disclosed in U.S. Pat. No. 4,222,143 are useful for cleaning large, irregular or concave surfaces adjacent wide interdental spaces, but cannot be used in the narrow gingival embrasures. Generally, the bristles are not stiff enough to exert sufficient pressure to remove plaque while thin enough to enter the interdental spaces. Again, the bristle tips present a potential for gingival damage.

As disclosed in the pending U.S. patent application Ser. No. 293,749 by Spademan, the tooth bristle cleansing head should have a shape, spacing and surface configuration for removing dental plaque from the interproximal embrasures and the exposed and subgingival surfaces of a tooth while minimizing damage to the gingival tissue facing the tooth and in the base of the sulcus.

SUMMARY OF THE INVENTION

In view of the foregoing, a principal object of the present invention is an improved toothbrush bristle cleansing head which has a shape, spacing and surface configuration for removing dental plaque from the exposed and subgingival surfaces of a tooth while minimizing damage to the gingival tissues facing the tooth and in the base of the sulcus.

A further object of the present invention is to provide a toothbrush bristle comprising a cleansing head which is rounded or blunted for presenting a nonabrasive surface to the gingival tissue surrounding a tooth.

Another object is to provide a toothbrush bristle with cleansing surface elements on the side of the bristle.

Still another object is to provide a toothbrush bristle cleansing element with a sharp edge for scraping tooth surfaces.

Still another object is a toothbrush bristle comprising an elongate, curved, flexible cleansing head, joined to a cylindrical section including shoulders to seat the cleansing head in a holder.

Still another object is a tooth bristle and mating holder that allows the bristle to rotate around its long axis.

Still another object is a tooth bristle and mating holder that allows the bristle to move in a slot in the holder.

Still another object is a tooth bristle and mating holder that allows the bristle cleansing surface elements to be offset from and directed toward the holder pivot axis.

Still another object is a tooth bristle that can be easily inserted into a mating holder.

BRIEF DESCRIPTION OF THE DRAWINGS

FIG. 1 is a front elevation of the cleansing surface of the bristle;

FIG. 2 is a side elevation of the bristle;

FIG. 2A is a side elevation of an alterrative embodiment of the bristle;

FIG. 3 is an enlarged detail of the cleansing head tip;

FIG. 4 is a cross-section along line 4—4 of FIG. 3;

FIG. 5 is an enlarged fragmentary top view of the bristle holder.

FIG. 6 is a view of the holder as in FIG. 5 with a collar inserted;

FIG. 7 is a sectional side view of the holder with a collar inserted;

FIG. 8 is a side elevation of a second embodiment of the bristle having two caps and a curved plate portion;

FIG. 9 is an end view of the bristle holder and a side view of the bristle in the embodiment of FIG. 8 being used to brush a tooth;

FIG. 10 is a front view of a third embodiment of the bristle;

FIG. 11 is a fragmentary sectional side view of a holder for the bristle of FIG. 10;

FIG. 12 is an end view of the holder of FIG. 11;

FIG. 13 is a top view of an alternative embodiment of the bristle of FIG. 10.

FIG. 14 is a fragmentary sectional bottom view of an alternative holder for the bristle of FIG. 13.

FIG. 15 is a fragmentary sectional side view of another alternative holder for the bristle of FIG. 10; and FIG. 16 is a fragmentary sectional bottom view of the bristle holder of FIG. 15 showing a portion of the mechanism for oscillating the holder.

DETAILED DESCRIPTION OF THE PREFERRED EMBODIMENT

Referring to FIGS. 1-4, the tooth cleansing means of the present invention comprises a single homogeneous bristle 10 molded from slightly flexible material such as nylon or polyethylene. Bristle 10 includes a generally elongated cleansing head 11 of a length in the range of one-half to twice the normal exposed height of a human tooth, and of a width less than that of a human tooth. However, the shape and size of the cleansing head may be varied to accomodate to various periodontal conditions. Cleansing head 11 has a cleansing surface 12 textured by polyhedral or conical cleansing elements 14 terminated by sharp edges 15. The bristle sides 15 and tip or end 18 are rounded to present a nonabrasive surface to the gingival surfaces surrounding teeth. A wall 17 around the periphery, of a lower height than the cleansing elements 14 so as not to interfere with their cleansing action, and the space between the cleansing elements, form pockets 13 to hold toothpaste. Its shape and spacing allows bristle 10 to penetrate the gingival sulci when the toothbrush handle 52 (FIG. 7) is held in the most common positions for brushing teeth. The bristle has a smooth back side 19. The shape of tip 18 minimizes gingival damage, and the cleansing action of elements 14 is more effective than conventional straight tubular bristles. Straight thin bristles work only when the brush handle is held within the range of a narrow cone having its point where the bristles contact the tooth, and do not work when the bristles are flexed. In contrast, bristle 10 may be preflexed to define a concave cleansing surface 75 as shown in FIG. 8, in order to maintain the cleansing surface in use flush against the tooth for the length of the bristle cleansing head.

Opposite tip end 18, bristle 10 has a stem 20 including a cylindrical portion 21 topped by a cap 22 having a diameter larger than that of the cylindrical portion. The cylindrical portion and cap allow bristle 10 to be rotatably connected to a bristle holder 50.

Referring to FIG. 2A in an alternative embodiment of the bristle 10, the stem 20 has an angulated segment 23 connecting the cylindrical portion 21 to the cleansing head 11. The angulated segment allows the bristle cleansing head cleansing elements to be offset from and directed toward the holder pivot axis during use. The bristle will self-align flush against the tooth more effectively than a bristle that has its long axis coaxial with the pivot axis in the holder.

Referring to FIGS. 5-7, tooth bristle holder 50 comprises an elongated body 51 with a flattened handle 52 and a smaller forward angulated portion 53. Forward portion 53 includes a retention tip 54 for holding the stem 20 of tooth bristle 10. Referring to FIG. 5, retention tip 54 comprises a gripping collar 55 with a slightly flexible wedge shaped opening 56. The forward portion 53 of holder 50 comprises a cylindrically shaped passage 57 which is slightly larger than the bristle's cylindrically shaped section 21. Extending away from passage 57, wedge shaped opening 56 allows cylindrically shaped section 21 of the bristle to be pressed from the tip end of portion 53 into cylindrical passage 57. To attach bristle 10, which is disposable, replaceable, and slightly flexible, it is pressed between the wedge shaped opening 56 until cylindrical section 21 is rotatably nested as a hinge pin in holder 50.

Referring to FIGS. 6 and 7, a sleeve 60 having collars 61 is preferably provided to help retain bristle 10 in passage 57. Sleeve 60 may be factory assembled by pressing it through opening 56. Bristle tip 18 is inserted into the bore of sleeve 60, and pressed by finger pressure on cap 22 down into the sleeve. A worn bristle 10 is removed by pushing upward on tip 18. This embodiment has the advantage of allowing bristle 10 to be inserted easily for replacement as necessary. Bristle 10 is held by friction against sleeve 60 but may rotate in holder 50 to follow the changing curvature of, and self-align against, the tooth surfaces as the holder is moved back and forth. Bristle 10 is rotated 180° to switch from brushing one side of the mouth to the other.

In an alternative embodiment, as shown in FIG. 8, a bristle 70 having a cylindrical portion 71 and a cap 72 is provided with a second cap 73 therebetween. Cap 73 is generally symmetrical about cylindrical portion 71 with respect to first cap 72. Bristle 70 is installed in holder 50, without sleeve 60, by pressing portion 71 through wedge shaped opening 56, with the caps 72 and 73 above and below passage 57, respectively. Bristle 70 then rotates in holder 50 to follow and self-align to the changing curvatures of the teeth. Bristle 70 is otherwise like bristle 10, having a cleansing surface 75 textured by polyhedral or conical cleansing elements 76, and having a concave curvature towards its cleansing surface 75, to maintain surface 75 against the tooth as explained above. Bristle 70 could as well be straight or have an angulated segment as shown in FIG. 2A and the other embodiments shown in FIGS. 1 and 10 could as well be curved. FIG. 9 is an end view of bristle 70 used in holder 50 to clean the subgingival surface 90 of a tooth 91. The curvature of concave surface 75 tends to balance the increasing bending movement applied by handle 50 from cylindrical portion 71 to tip 78 of bristle 70. Tip 78 enters the subgingival space and is held flush against surface 90 of tooth 91.

In a third embodiment illustrated by FIG. 10, a bristle 100 has a cleansing head portion 99 divided into two digits 103, and a cylindrical portion 101 ending in a cylindrical cap 102. Bristle 100 is inserted into a holder 110 (FIGS. 11-12) through channel 106 into a chamber 117 having a diameter slightly larger than cap 102. Chamber 117 is closed at the top 114, and at the bottom opens out through a neck 111 having a diameter slightly larger than cylindrical portion 101 of bristle 100. Bristle 100 swivels in its handle similarly to bristles 10 and 70 in the other embodiments.

Referring to FIG. 13 in an alternative embodiment of the bristle 100, the cap 102 has flatened portions 104 that allow the bristle to move and slide in a complimentary curved slot 113 in a holder 112 as shown in FIG. 14. The flatened sections 104 allow the bristle 100 cleansing head cleansing elements to be offset from and directed toward the holder pivot axis during use. Slot 113 is closed at the top and at the bottom opens out through a neck 115 having a diameter only slightly larger than the cylindrical portion 101 of bristle 100. Bristle 100 is inserted into holder 112 by slight compression of the plastic cap 102 formed of high density polyethylene or the like.

In an alternative embodiment as shown in FIGS. 15 and 16 of a holder 120 for holding the bristle 100 of FIG. 10, one end of an arm 121 hinge pin 122 is rotatably secured in a bore 123 in holder 120 by a factory assembled press fit peg 124. Bore 123 has a diameter slightly larger than the hinge pin 122. A resilient force unit such as a compression coil spring 125 may be loaded on hinge pin 122 to distribute the load during insertion and movement of the bristle in the gingival sulcus. For special cleansing applications, a bar 127 having serrations along a portion of its length can be slidably engaged by a slot 128 in handle 120 and mesh with complimentary serrations on hinge pin 122 such that by sliding the bar 127 relative to the handle 120 the movement of arm 121 is controlled to a selected position. The portion of the bar not having serration may interface with the hinge pin to form an adjustable friction fit. In the opposite end of arm 121 from hinge pin 122, the arm 121 has a bore 126. Bristle 100 cylindrical cap 102 of FIG. 10 is press fit into bore 126 or may be keyed to retain bristle 100 in a facing relationship to the rotation axis of hinge pin 122. A second bore 126 may be located in arm 121 to hold a second bristle. Each bore may include a resilient force unit to individually spring load the bristles. The pivoting arm 121 allows the bristle cleansing head cleansing elements to be offset from and directed toward the hinge pin 122 rotation axis. This bristle and holder will more readily self-align the bristle cleansing head cleansing elements flush against the tooth than a conventional bristle and holder. With the operator pulling the bristle cleansing head against the tooth surface, there is enhanced removal of plaque from the exposed and subgingival surface of the tooth while protecting the gingiva surrounding the tooth and in the gingival sulcus.

Holder 120 has section 129 and section 130. Extending from the center of section 129 is a dovetail shaped tongue member 131 for fitting in slidable engagement in a corresponding shaped groove 132 provided therefore in section 130. In the holder there is provided a rectangular cavity 133. Mounted in the cavity, there is provided a pair of electrically conductive reed members 134 and 135. One end of reed member 134 is attached to holder section 130. by means of post 136. In operation electrical signals are applied to reed members 134 and 135 in a conventional manner such that reed member 134 moves in an oscillatory manner relative to reed member 135. The holder section 130 attached to the end of reed member 134 is caused to move a corresponding distance. It has been found that the tooth bristle should oscillate in a short excursion of approximately 2 millimeters. With the bristle 100 attached to the handle, the oscillatory motion results in greatly enhanced cleansing of the surface of the tooth when the bristle head is located in the gingival sulcus without damaging the gingival tissue facing the tooth and in the base of the sulcus.

Details have been disclosed to illustrate the invention in a preferred embodiment of which adaptions and modifications within the spirit and a scope of the invention will occur to those skilled in the art. The scope of the invention is limited only by the following claims.

I claim:

1. A tooth cleansing bristle in combination with a tooth bristle holder comprising a stem rotatably movably engageable during use with the holder, means resiliently biasing a portion of the bristle towards the holder, and an elongated cleansing head connected to the stem having a first rounded end and a smooth first side surface adjacent the end to protect against injury to subgingival surfaces surrounding the tooth to be cleansed, said cleansing head including a second side surface adjacent the rounded end and subatantially opposite to the first side surface, the second surface having abrasive cleansing means distributed over at least a part of the length thereof, said cleansing means surface being textured by polyhedral cleansing elements, wherein said second surface is provided with a peripheral wall having a lower height relative to said second surface than said cleansing elements, said wall being rounded to be nonabrasive to the subgingival surfaces.

2. A tooth cleansing bristle as in claim 1 wherein said cleansing means comprises cleansing elements terminating in relatively sharp cleansing element ends.

3. A tooth cleansing bristle as in claim 2 wherein said cleansing means includes means for holding cleansing compound in the vicinity of the cleansing elements.

4. A tooth cleansing bristle as in claim 3 wherein said holding means comprises depressions located adjacent the cleansing elements.

5. A tooth cleansing bristle as in claim 1 wherein said stem forms a hinge pin allowing said bristle to be engageable with the holder with the axis of said holder rotatable relative to the bristle in a plane substantially normal to said smooth first side surface of said cleansing head.

6. A tooth cleansing bristle as in claim 5 wherein said stem extends along a long axis of said cleansing head.

7. A tooth cleansing bristle as in claim 6 wherein said stem includes a cylindrical portion and, on the opposite side of said cylindrical portion from said cleansing head; a cap portion having a larger diameter than said cylindrical portion.

8. A tooth cleansing bristle as in claim 1 and curved to define a concave cleansing means surface.

9. A tooth cleansing bristle in combination with a tooth bristle holder comprising a stem rotatably movably engageable during use with the holder, means resiliently biasing a portion of the bristle towards the holder, and an elongated cleansing head connected to the stem having a first rounded end and a smooth first side surface adjacent the end to protect against injury to subgingival surfaces surrounding the tooth to be cleansed, said stem forming a hinge pin allowing said bristle to be engageable with the holder with the axis of said holder rotatable relative to the bristle in a plane substantially normal to said smooth first side surface of said cleansing head, said stem extending along a axis of said cleansing head, said stem including a cylindrical portion and, on the opposite side of said cylindrical portion form said cleansing head; a cap portion having a larger diameter than said cylindrical portion, said holder having:

a cylindrical opening rotatably engageable with said stem; and a channel extending from said cylindrical opening along an axis of said holder to a tip end of said holder, said channel having a cross-section, perpendicular to said holder axis, slightly smaller than the diameter of said opening.

10. A tooth cleansing bristle and holder as in claim 9 wherein:

said cylindrical opening comprises a chamber inside said holder, closed at one end, having a diameter slightly larger than that of said cap; and a neck, of a diameter slightly larger than that of the cylindrical portion of said stem, between said chamber and the outside of said holder; and said holder also has a channel, extending from the chamber and neck out to the tip of the holder, whereby said bristle may be inserted into said holder by positioning said cap and said cylindrical portion of said bristle in said channel at the tip of the holder, and pressing said bristle into and through said channel to seat said cap in said chamber and said cylindrical portion of said stem, respectively.

11. A tooth cleansing bristle and holder as in claim 10 wherein said cylindrical opening has a diameter slightly larger than said neck, and extends through said holder.

12. A tooth cleansing bristle and holder as in claim 11 wherein said channel converges from said tip end of said holder towards said cylindrical opening in said holder.

13. A tooth cleansing bristle and holder as in claim 12 wherein said stem has a second cap portion disposed between said cylindrical portion and said cleansing head portion, said second cap being generally symmetrical, about said cylindrical portion, with respect to the first mentioned cap.

14. A tooth cleansing bristle and holder as in claim 12 and further including a circular cylindrical sleeve disposed in said cylindrical opening, said sleeve terminating in first and second collars abutting outside surfaces of said holder at opposite ends of said cylindrical opening, whereby said bristle inserted in said sleeve is held rotatably with slight friction.

15. A tooth cleansing bristle comprising a stem rotatably movably engageable with a tooth bristle holder about an axis of rotation and an elongated cleansing head having abrasive cleansing means distributed over at least a part of the length thereof, said cleansing means being offset from and directed toward the axis of rotation of said stem in said holder.

16. A tooth cleansing bristle as in claim 15 wherein said stem is slidably engageable with said tooth bristle holder.

17. A tooth cleansing bristle as in claim 15 wherein said cleansing head is divided into at least two digits.

18. A tooth cleansing bristle as in claim 15 wherein said cleansing head includes a first rounded end to protect against injury to subgingival surfaces surrounding the tooth to be cleansed.

19. The combination of a tooth cleansing bristle as in claim 15 and a holder having:

an arm movably engageable with said holder, said arm having means for engaging said stem.

20. A tooth cleansing bristle and holder as in claim 15 wherein said means for engaging said stem comprises a bore.

21. A tooth cleansing bristle and holder as in claim 19 wherein said arm is resiliently biased against said holder.

22. A tooth cleansing bristle and holder as in claim 15 wherein said holder comprises a means for oscillating said bristle relative to said holder.

23. A tooth cleansing bristle as in claim 15 wherein said cleansing head includes a first rounded end and a smooth first side surface adjacent the end to protect against injury to subgingival surfaces surrounding the tooth to be cleansed.

24. A tooth cleansing bristle and holder as in claim 15 wherein said holder comprises means for controlling movement of said bristle stem relative to said holder.

* * * * *